United States Patent [19]

James, Jr. et al.

[11] Patent Number: 5,013,424

[45] Date of Patent: May 7, 1991

[54] PROCESS FOR THE SIMULTANEOUS HYDROGENATION OF A FIRST FEEDSTOCK COMPRISING HYDROCARBONACEOUS COMPOUNDS AND HAVING A NON-DISTILLABLE COMPONENT AND A SECOND FEEDSTOCK COMPRISING HALOGENATED ORGANIC COMPOUNDS

[75] Inventors: Robert B. James, Jr., Northbrook; Tom N. Kalnes, La Grange; Steven P. Lankton, Wheeling, all of Ill.

[73] Assignee: UOP, Des Plaines, Ill.

[21] Appl. No.: 559,820

[22] Filed: Jul. 30, 1990

[51] Int. Cl.$^5$ .............................................. C07C 15/02

[52] U.S. Cl. .................................. 208/78; 208/262.1; 208/262.5; 208/144; 208/145; 208/85; 585/310; 585/320; 585/469; 585/733

[58] Field of Search .................. 208/262.1, 262.5, 144, 208/143; 585/310, 320, 469, 733

[56] References Cited

U.S. PATENT DOCUMENTS

| | | | |
|---|---|---|---|
| 4,895,995 | 1/1990 | James, Jr. et al. | 208/262.5 |
| 4,899,001 | 2/1990 | Kalnes et al. | 208/262.5 |
| 4,902,842 | 2/1990 | Kalnes et al. | 208/262.5 |
| 4,923,590 | 5/1990 | Kalnes et al. | 208/262.5 |
| 4,929,781 | 5/1990 | James, Jr. et al. | 208/262.5 |

*Primary Examiner*—Helane E. Myers
*Attorney, Agent, or Firm*—Thomas K. McBride; John G. Tolomei; John G. Cutts, Jr.

[57] ABSTRACT

A process for the production of hydrogenated, distillable hydrocarbonaceous product from a feed comprising hydrocarbonaceous compounds and having a non-distillable component, and a feed comprising halogenated organic compounds by means of contacting the feed comprising hydrocarbonaceous compounds and having a non-distillable component with a hot hydrogen-rich gaseous stream to increase the temperature of this feed stream to vaporize at least a portion of the distillable hydrocarbonaceous compounds thereby producing a distillable hydrocarbonaceous product which is immediately hydrogenated in an integrated hydrogenation zone. The feed comprising halogenated organic compounds is contacted in a second hydrogenated hydrocarbonaceous product and at least one water-soluble inorganic halide compound.

18 Claims, 1 Drawing Sheet

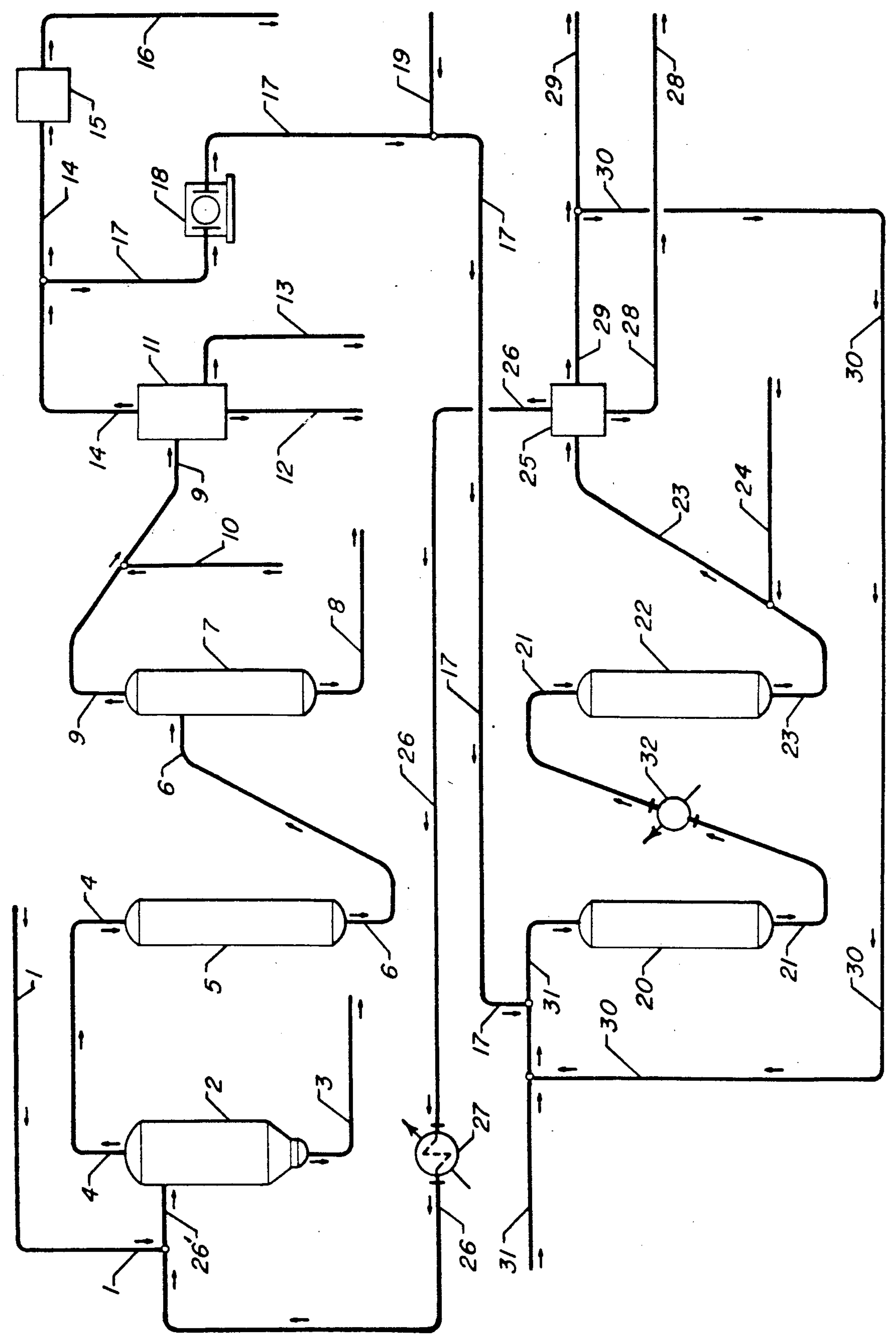
1
2
3
4
5
6
7
8
9
10
11
12
13
14
15
16
17
18
19
20
21
22
23
24
25
26
26'
27
28
29
30
31
32

PROCESS FOR THE SIMULTANEOUS HYDROGENATION OF A FIRST FEEDSTOCK COMPRISING HYDROCARBONACEOUS COMPOUNDS AND HAVING A NON-DISTILLABLE COMPONENT AND A SECOND FEEDSTOCK COMPRISING HALOGENATED ORGANIC COMPOUNDS

BACKGROUND OF THE INVENTION

The field of art to which this invention pertains is the production of hydrogenated distillable hydrocarbonaceous compounds from a hydrocarbonaceous feed having a non-distillable component and a feed comprising halogenated organic compounds.

More specifically, the invention relates to a process for the simultaneous hydrogenation of a first feedstock comprising hydrocarbonaceous compounds and having a non-distillable component, and a second feedstock comprising halogenated organic compounds which process comprises: (a) contacting the first feedstock with a first hydrogen-rich gaseous stream having a temperature greater than the first feedstock in a flash zone at flash conditions thereby increasing the temperature of the first feedstock and vaporizing at least a portion thereof to provide a hydrocarbonaceous vapor stream comprising hydrogen, and a heavy product comprising the non-distillable component; (b) contacting the hydrocarbonaceous vapor stream comprising hydrogen with a hydrogenation catalyst in a first hydrogenation reaction zone at hydrogenation conditions to increase the hydrogen content of the hydrocarbonaceous compounds contained in the hydrocarbonaceous vapor stream; (c) condensing at least a portion of the resulting effluent from the first hydrogenation reaction zone to produce a second hydrogen-rich gaseous stream and a first liquid hydrogenated stream comprising hydrogenated distillable hydrocarbonaceous compounds; (d) reacting the second feedstock comprising halogenated organic compounds and at least a portion of the second hydrogen-rich gaseous stream with a hydrogenation catalyst in a second hydrogenation reaction zone at hydrogenation conditions selected to produce hydrocarbonaceous compounds and at least one water-soluble inorganic halide compound; (e) contacting the resulting effluent from the second hydrogenation zone containing hydrocarbonaceous compounds and at least one water-soluble inorganic halide compound with a halide-lean aqueous scrubbing solution; (f) introducing a resulting admixture of the effluent from the second hydrogenation zone and the halide-lean aqueous scrubbing solution into a separation zone to provide a third hydrogen-rich gaseous stream, a second liquid hydrogenated stream comprising hydrocarbonaceous compounds and a halide-rich aqueous scrubbing solution containing at least a portion of the water-soluble inorganic halide compound; (g) recycling and heating at least a portion of the third hydrogen-rich gaseous stream recovered in step (f) into step (a) as at least a portion of the first hydrogen-rich gaseous stream; and (h) recovering the first liquid hydrogenated stream comprising hydrogenated distillable hydrocarbonaceous compounds from step (c) and the second liquid hydrogenated stream comprising hydrocarbonaceous compounds from step (f).

There is a steadily increasing demand for technology which is capable of the simultaneous hydrogenation of a first feedstock comprising hydrocarbonaceous compounds and having a non-distillable component and a second feedstock comprising halogenated organic compounds. Previous techniques utilized to dispose of such feedstocks which are often undesirable waste effluents such as used lubricating oils and spent solvents, for example, have frequently become environmentally unpopular or illegal and, in general, have always been expensive. With the increased environmental emphasis for the treatment and recycle of chlorinated organic product and waste oils, there is an increased need for the conversion of these products in the event that they become unwanted or undesirable. For example, during the disposal or recycle of potentially environmentally harmful halogenated organic waste streams, an important step in the total solution to the problem is the conditioning of the halogenated organic stream which facilitates the ultimate resolution to provide product streams which may be handled in an environmentally acceptable manner. In another example, large quantities of used motor oil are generated and discarded which oil would provide a large potential supply of feedstock for the present invention while providing an environmentally responsible disposal. Therefore, those skilled in the art have sought to find feasible techniques to convert such feedstocks to provide hydrocarbonaceous product streams which may be safely and usefully employed or recycled. Previous techniques which have been employed include incineration which, in addition to potential pollution considerations, fails to recover valuable hydrocarbonaceous materials.

INFORMATION DISCLOSURE

In U.S. Pat. No. 3,592,864 (Gewartowski), a process is disclosed for hydrogenating benzene to form cyclohexane utilizing once-through hydrogen-containing gas wherein the exothermic heat of reaction is utilized as the sole source of heat input to steam generation means and wherein the processing system is enhanced by the elimination of recycle gas compressors, treaters, coolers and heaters.

In U.S. Pat. No. 3,133,013 (Watkins), a process is disclosed which relates to the hydrorefining of hydrocarbons for the purpose of removing diverse contaminants therefrom and/or reacting such hydrocarbons to improve the chemical and physical characteristics thereof. In addition, the process is directed toward the selective hydrogenation of unsaturated, coke-forming hydrocarbons through the use of particular conditions whereby the formation of coke, otherwise resulting from the hydrorefining of such hydrocarbon fractions and distillates, is effectively inhibited.

In U.S. Pat. No. 3,992,285 (Hutchings), a process is disclosed for the desulfurization of a hydrocarbonaceous black oil containing sulfur and asphaltic material which comprises preheating the oil by indirect heat exchange to a temperature not in excess of about 550° F., commingling the preheated oil with a steam-containing gas to raise the temperature of the oil to a desulfurization temperature of about 600° F. to about 800° F. and contacting the thus heated oil at hydrocarbon conversion conditions with a desulfurization catalyst.

BRIEF SUMMARY OF THE INVENTION

The invention provides an improved process for the production of hydrogenated, distillable hydrocarbonaceous product from a feed comprising hydrocarbonaceous compounds and having a non-distillable component, and a feed comprising halogenated organic compounds by means of contacting the feed comprising hydrocarbonaceous compounds and having a non-distillable component with a hot hydrogen-rich gaseous stream to increase the temperature of this feed stream to vaporize at least a portion of the distillable hydrocarbonaceous compounds thereby producing a distillable hydrocarbonaceous product which is immediately hydrogenated in an integrated hydrogenation zone. The feed comprising halogenated organic compounds is contacted in a second hydrogenation zone at hydrogenation conditions to produce a hydrogenated hydrocarbonaceous product and at least one water-soluble inorganic halide compound. Important elements of the process are the integrated hydrogenation reaction zones which reduce capital and utility costs, and the recycle of the hydrogen-rich gas stream from the second hydrogenation zone. This gas stream may contain small quantities of unconverted volatile organic halide compounds and the first hydrogenation zone serves to ensure complete destruction of these compounds. The consecutive passage of this gas stream through both a thermal zone for heating the gas stream followed by a catalytic hydrogenation zone will convert greater than 99% of the organic halide compounds to hydrogen halide.

One embodiment of the invention may be characterized as a process for the simultaneous hydrogenation of a first feedstock comprising hydrocarbonaceous compounds and having a non-distillable component, and a second feedstock comprising halogenated organic compounds which process comprises: (a) contacting the first feedstock with a first hydrogen-rich gaseous stream having a temperature greater than the first feedstock in a flash zone at flash conditions thereby increasing the temperature of the first feedstock and vaporizing at least a portion thereof to provide a hydrocarbonaceous vapor stream comprising hydrogen, and a heavy product comprising the non-distillable component; (b) contacting the hydrocarbonaceous vapor stream comprising hydrogen with a hydrogenation catalyst in a first hydrogenation reaction zone at hydrogenation conditions to increase the hydrogen content of the hydrocarbonaceous compounds contained in the hydrocarbonaceous vapor stream; (c) condensing at least a portion of the resulting effluent from the first hydrogenation reaction zone to produce a second hydrogen-rich gaseous stream and a first liquid hydrogenated stream comprising hydrogenated distillable hydrocarbonaceous compounds; (d) reacting the second feedstock comprising halogenated organic compounds and at least a portion of the second hydrogen-rich gaseous stream with a hydrogenation catalyst in a second hydrogenation reaction zone at hydrogenation conditions selected to produce hydrocarbonaceous compounds and at least one water-soluble inorganic halide compound; (e) contacting the resulting effluent from the second hydrogenation zone containing hydrocarbonaceous compounds and at least one water-soluble inorganic halide compound with a halide-lean aqueous scrubbing solution; (f) introducing a resulting admixture of the effluent from the second hydrogenation zone and the halide-lean aqueous scrubbing solution into a separation zone to provide a third hydrogen-rich gaseous stream, a second liquid hydrogenated stream comprising hydrocarbonaceous compounds and a halide-rich aqueous scrubbing solution containing at least a portion of the water-soluble inorganic halide compound; (g) recycling and heating at least a portion of the third hydrogen-rich gaseous stream recovered in step (f) into step (a) as at least a portion of the first hydrogen-rich gaseous stream; and (h) recovering the first liquid hydrogenated stream comprising hydrogenated distillable hydrocarbonaceous compounds from step (c) and the second liquid hydrogenated stream comprising hydrocarbonaceous compounds from step (f).

Other embodiments of the present invention encompass further details such as preferred feedstocks, hydrogenation catalysts, aqueous scrubbing solutions and operating conditions, all of which are hereinafter disclosed in the following discussion of each of these facets of the invention.

BRIEF DESCRIPTION OF THE DRAWING

The drawing is a simplified process flow diagram of a preferred embodiment of the present invention.

DETAILED DESCRIPTION OF THE INVENTION

The present invention provides an improved integrated process for the simultaneous hydrogenation of a first feedstock comprising hydrocarbonaceous compounds and having a non-distillable component, and a second feedstock comprising halogenated organic compounds.

A wide variety of hydrocarbonaceous streams having a non-distillable component are to be candidates for feedstock in accordance with the process of the present invention. Examples of such hydrocarbonaceous streams which are suitable for treatment by a process of the present invention are dielectric fluids, hydraulic fluids, heat transfer fluids, used lubricating oil, used cutting oils, used solvents, still bottoms from solvent recycle operations, coal tars, atmospheric residuum, oils contaminated with polychlorinated biphenyls (PCB), and other hydrocarbonaceous industrial waste. Many of these hydrocarbonaceous streams may contain non-distillable components which include, for example, organometallic compounds, inorganic metallic compounds, finely divided particulate matter and non-distillable hydrocarbonaceous compounds. The present invention is particularly advantageous when the non-distillable components comprise sub-micron particulate matter and the conventional techniques of filtration or centrifugation tend to be highly ineffective.

The presence of a non-distillable component including finely divided particulate matter in a hydrocarbonaceous feed to a hydrogenation zone greatly increases the difficulty of hydrogenation. A non-distillable component tends (1) to foul the hot heat exchange surfaces which are used to heat the feed to hydrogenation conditions, (2) to form coke or in some other manner deactivate the hydrogenation catalyst thereby shortening its active life and (3) to otherwise hinder a smooth and facile hydrogenation operation. Particulate matter in a feed stream tends to deposit within the hydrogenation zone and to plug a fixed hydrogenation catalyst bed thereby abbreviating the time on stream.

Once the hydrocarbonaceous feed stream containing a non-distillable component is separated into a distillable hydrocarbonaceous stream and a heavy non-distillable product, the resulting distillable hydrocarbonaceous stream is introduced into a hydrogenation zone. If the feed stream contains metallic compounds such as those that contain metals such as zinc, copper, iron, barium, phosphorous, magnesium, aluminum, lead, mercury, cadmium, cobalt, arsenic, vanadium, chromium, and nickel, these compounds will be isolated in the relatively small volume of recovered non-distillable product which may then be treated for metals recovery or otherwise disposed of as desired. In the event that the feed stream contains distillable hydrocarbonaceous compounds which include sulfur, oxygen, nitrogen, metal or halogen components, the resulting recovered distillable hydrocarbonaceous stream is hydrogenated to remove or convert such components as desired. In a preferred embodiment of the present invention, the hydrogenation of the resulting distillable hydrocarbonaceous stream is preferably conducted immediately without intermediate separation or condensation. The advantages of the integrated process of the present invention will be readily apparent to those skilled in the art and include the economy of greatly reduced utility costs.

In accordance with the present invention, a hydrocarbonaceous stream containing a non-distillable component is contacted with a hot hydrogen-rich gaseous stream having a temperature greater than the hydrocarbonaceous stream in a flash zone at flash conditions thereby increasing the temperature of the hydrocarbonaceous stream and vaporizing at least a portion thereof to provide a hydrocarbonaceous vapor stream comprising hydrogen and a heavy non-distillable product. The hot hydrogen-rich gaseous stream preferably comprises more than about 70 mol. % hydrogen and preferably more than about 90 mol. % hydrogen. In a preferred embodiment, the hot hydrogen-rich gaseous stream is comprised of a recycle hydrogen gas stream which contains trace quantities of halogenated organic compounds.

The hot hydrogen-rich gaseous stream is multi-functional and serves as (1) a heat source used to directly heat the hydrocarbonaceous feed stream to preclude the coke formation that could otherwise occur when using an indirect heating apparatus such as a heater or heat-exchanger, (2) a diluent to reduce the partial pressure of the hydrocarbonaceous compounds during vaporization in the flash zone, (3) a possible reactant to minimize the formation of hydrocarbonaceous polymers at elevated temperatures, (4) a stripping medium, and (5) at least a portion of the hydrogen required in the hydrogenation reaction zone. In addition, when the hot hydrogen-rich gaseous stream is composed of a recycle hydrogen gas stream which contains halogenated organic compounds, the subsequent thermal and catalytic zones through which this stream passes is a valuable technique to ensure essentially complete conversion of halogenated organic compounds in the present process. In accordance with the present invention, the hydrocarbonaceous feed stream containing a non-distillable component is preferably maintained at a temperature less than about 482° F. (250° C.) before being introduced into the flash zone in order to prevent or minimize the thermal degradation of the feed stream. Depending upon the characteristics and composition of the hydrocarbonaceous feed stream, the hot hydrogen-rich gaseous stream is introduced into the flash zone at a temperature greater than the hydrocarbonaceous feed stream and preferably at a temperature from about 200° F. (93° C.) to about 1200° F. (649° C).

The flash zone is preferably maintained at flash conditions which include a temperature from about 150° F. (65° C.) to about 860° F. (460° C.), a pressure from about atmospheric to about 2000 psig (13788 kPa gauge), a hydrogen circulation rate of about 1000 SCFB (168 normal $m^3/m^3$) to about 60,000 SCFB (10,110 normal $m^3/m^3$) based on the hydrocarbonaceous feed stream to the flash zone and an average residence time of the hydrogen-containing, hydrocarbonaceous vapor stream in the flash zone from about 0.1 seconds to about 50 seconds. A more preferred average residence time of the hydrogen-containing hydrocarbonaceous vapor stream in the flash zone is from about 1 second to about 10 seconds.

The resulting heavy non-distillable portion of the feed stream is removed from the bottom of the flash zone as required to yield a heavy non-distillable product. The heavy non-distillable product may contain a relatively small amount of distillable components, but since essentially all of the non-distillable components contained in the hydrocarbonaceous feed stream are recovered in this product stream, the term "heavy non-distillable product" is nevertheless used for the convenient description of this product stream. The heavy non-distillable product preferably contains a distillable component of less than about 10 weight percent and more preferably less than about 5 weight percent. Under certain circumstances with a feed stream not having an appreciable amount of liquid non-distillable components, it is contemplated that an additional liquid may be utilized to flush the heavy non-distillables from the flash zone. An example of this situation is when the hydrocarbonaceous feed stream comprises a very high percentage of distillable hydrocarbonaceous compounds and relatively small quantities of finely divided particulate matter "solid" and essentially no liquid non-distillable component for use as a carrier for the solids. Such a flush liquid may, for example, be a high boiling range vacuum gas oil having a boiling range from about 700° F. (371° C.) to about 1000° F. (538° C.) or a vacuum tower bottom stream boiling at a temperature greater than about 1000° F. (538° C.). In the event when the non-distillable fraction is flushed with vacuum resid (bitumen), the properties of the resid are enhanced for use as an asphalt cement and thus provides a useful outlet for the bottoms. In addition, toxic metals are stabilized and made non-leachable. The selection of a flush liquid depends upon the composition of the hydrocarbonaceous feed stream and the prevailing flash conditions in the flash separator, and the volume of the flush liquid is preferably limited to that required for removal of the heavy non-distillable component.

The resulting hydrogen-containing hydrocarbonaceous vapor stream is removed from the flash zone and is introduced into a catalytic hydrogenation zone containing hydrogenation catalyst and maintained at hydrogenation conditions. The catalytic hydrogenation zone may contain a fixed, ebullated or fluidized catalyst bed. This reaction zone is preferably maintained under an imposed pressure from about atmospheric (0 kPa gauge) to about 2000 psig (13790 kPa gauge) and more preferably under a pressure from about 100 psig (689.5 kPa gauge) to about 1800 psig (12411 kPa gauge). Suitably, such reaction is conducted with a maximum catalyst bed temperature in the range of about 122° F. (50° C.) to about 850° F. (454° C.) selected to perform the desired hydrogenation conversion to reduce or eliminate the undesirable characteristics or components of the hydrocarbonaceous vapor stream. In accordance with the present invention, it is contemplated that the desired hydrogenation conversion includes, for example, dehalogenation, desulfurization, denitrification, olefin saturation, oxygenate conversion and hydrocracking. Further preferred operating conditions include liquid hourly space velocities in the range from about 0.05 hr.$^{31\ 1}$ to about 20 hr.$^{31\ 1}$ and hydrogen circulation rates from about 200 standard cubic feet per barrel (SCFB) (33.71 normal $m^3/m^3$) to about 70,000 SCFB (11,796 normal $m^3/m^3$), preferably from about 300 SCFB (50.6 normal $m^3/m^3$) to about 20,000 SCFB (3371 normal $m^3/m^3$).

In the event that the temperature of the hydrogen-containing hydrocarbonaceous stream which is removed from the flash zone is not deemed to be exactly the temperature selected to operate the catalytic hydrogenation zone, we contemplate that the temperature of the hydrogen-containing, hydrocarbonaceous stream may be adjusted either upward or downward in order to achieve the desired temperature in the catalytic hydrogenation zone. Such a temperature adjustment may be accomplished, for example, by the addition of either cold or hot hydrogen.

The preferred catalytic composite disposed within the hereinabove-described hydrogenation zone can be characterized as containing a metallic component having hydrogenation activity, which component is combined with a suitable refractory inorganic oxide carrier material of either synthetic or natural origin. The precise composition and method of manufacturing the carrier material are not considered essential to the present invention. Preferred carrier materials are alumina, silica and mixtures thereof. Suitable metallic components having hydrogenation activity are those selected from the group comprising the metals of Groups VI-B and VIII of the Periodic Table, as set forth in the *Periodic Table of the Elements*, E.H. Sargent and Company, 1964. Thus, the catalytic composites may comprise one or more metallic components from the group of molybdenum, tungsten, chromium, iron, cobalt, nickel, platinum, palladium, iridium, osmium, rhodium, ruthenium, and mixtures thereof. The concentration of the catalytically active metallic component, or components, is primarily dependent upon a particular metal as well as the physical and/or chemical characteristics of the particular hydrocarbon feedstock. For example, the metallic components of Group VI-B are generally present in an amount within the range of from about 1 to about 20 weight percent, the iron-group metals in an amount within the range of about 0.2 to about 10 weight percent, whereas the noble metals of Group VIII are preferably present in an amount within the range of from about 0.1 to about 5 weight percent, all of which are calculated as if these components existed within the catalytic composite in the elemental state. In addition, any catalyst employed commercially for hydrogenating middle distillate hydrocarbonaceous compounds to remove nitrogen and sulfur may function effectively in the hydrogenation zone of the present invention. It is further contemplated that hydrogenation catalytic composites may comprise one or more of the following components: cesium, francium, lithium, potassium, rubidium, sodium, copper, gold, silver, cadmium, mercury and zinc.

The hydrocarbonaceous effluent from the hydrogenation zone is preferably partially condensed in a hot separator and then contacted with an aqueous scrubbing solution and the admixture is admitted to a separation zone in order to separate a spent aqueous stream, a hydrogenated hydrocarbonaceous liquid phase and a hydrogen-rich gaseous phase. The contact of the hydrocarbonaceous effluent from the hydrogenation zone with the aqueous scrubbing solution may be performed in any convenient manner and is preferably conducted by cocurrent, in-line mixing which may be promoted by inherent turbulence, mixing orifices or any other suitable mixing means. The aqueous scrubbing solution is preferably introduced in an amount from about 1 to about 100 volume percent based on the hydrocarbonaceous effluent from the hydrogenation zone. The aqueous scrubbing solution is selected depending on the characteristics of the hydrocarbonaceous vapor stream introduced into the hydrogenation zone. For example, if the hydrocarbonaceous vapor stream to the hydrogenation zone comprises halogenated compounds, the aqueous scrubbing solution preferably contains a basic compound such as calcium hydroxide, potassium hydroxide, potassium carbonate, sodium carbonate or sodium hydroxide in order to neutralize the acid such as hydrogen chloride, hydrogen bromide and hydrogen fluoride, for example, which is formed during the hydrogenation of the halogen compounds. In the event that the hydrocarbonaceous vapor stream contains only sulfur and nitrogen compounds, water may be a suitable aqueous scrubbing solution to dissolve the resulting hydrogen sulfide and ammonia. The resulting hydrogenated hydrocarbonaceous liquid phase is recovered and the hydrogen-rich gaseous phase may be recycled to the hydrogenation zone if desired.

The resulting hydrogenated hydrocarbonaceous liquid phase is preferably recovered from the hydrogen-rich gaseous phase in a separation zone which is maintained at essentially the same pressure as the hydrogenation reaction zone and as a consequence contains dissolved hydrogen and low molecular weight normally gaseous hydrocarbons if present. In accordance with the present invention, it is preferred that the hydrogenated hydrocarbonaceous liquid phase comprising the hereinabove mentioned gases be stabilized in a convenient manner, such as, for example, by stripping or flashing to remove the normally gaseous components to provide a stable hydrogenated distillable hydrocarbonaceous product.

A wide variety of halogenated organic compounds, both unsaturated and saturated, are candidates for a feedstock in accordance with the process of the present invention. Examples of organic streams comprising halogenated organic compounds which are suitable for treatment by the process of the present invention are dielectric fluids, hydraulic fluids, heat transfer fluids, used lubricating oil, used cutting oils, used solvents, halogenated hydrocarbonaceous by-products, oils contaminated with polychlorinated biphenyls (PCB), halogenated wastes, petrochemical by-products and other halogenated hydrocarbonaceous industrial waste. The halogenated organic feed streams which are contemplated for use in the present invention may also contain organic compounds which include sulfur, oxygen, nitrogen or metal components which may be hydrogenated to remove or convert such components as desired. The halogenated organic compounds may also contain hydrogen and are therefore then referred to as hydrocarbonaceous compounds.

Preferred feedstocks comprise fractionation column bottoms in the production of allyl chloride, fractionation column bottoms in the production of ethylene dichloride, fractionation column bottoms in the production of trichloroethylene and perchloroethylene, used dielectric fluid containing polychlorinated biphenyls (PCB) and chlorinated benzene, used chlorinated solvents, and mixtures thereof.

Other preferred feedstocks containing halogenated organic compounds comprise fractionation bottoms from the purification column in epichlorohydrin production, carbon tetrachloride, 1, 1, 1-trichloroethane, chlorinated alcohols, chlorinated ethers, chlorofluorocarbons, ethylene dibromide and admixtures thereof.

The halogenated organic compounds which are contemplated as feedstocks in the present invention preferably contain a halogen selected from the group consisting of chlorine, fluorine and bromine.

In accordance with the present invention, a feedstock comprising halogenated organic compounds is introduced in admixture with a hydrogen-rich gaseous stream into a catalytic hydrogenation zone containing hydrogenation catalyst and maintained at hydrogenation conditions. This catalytic hydrogenation zone may contain a fixed, ebullated or fluidized catalyst bed. The operating conditions selected for this catalytic hydrogenation zone are selected primarily to dehalogenate the halogenated organic compounds which are introduced thereto. This catalytic hydrogenation zone is preferably maintained under an imposed pressure from about atmospheric (0 kPa gauge) to about 2000 psig (13790 kPa gauge) and more preferably under a pressure from about 100 psig (689.5 kPa gauge) to about 1800 psig (12411 kPa gauge). Suitably, such reaction is conducted with a maximum catalyst bed temperature in the range of about 122° F. (50° C.) to about 850° F. (454° C.) selected to perform the desired hydrogenation and dehalogenation conversion to reduce or eliminate the concentration of halogenated organic compounds contained in the combined feed stream. In accordance with the present invention, it is contemplated that the desired hydrogenation conversion includes, for example, dehalogenation, desulfurization, denitrification, olefin saturation, oxygenate conversion and hydrocracking. Further preferred operating conditions include liquid hourly space velocities in the range from about 0.05 hr.$^{31\ 1}$ to about 20 hr.$^{31\ 1}$ and hydrogen circulation rates from about 200 standard cubic feet per barrel (SCFB) (33.71 normal $m^3/m^3$) to about 100,000 SCFB (16851 normal $m^3/m^3$), preferably from about 200 SCFB (33.71 normal $m^3/m^3$) to about 50,000 SCFB (8427 normal $m^3/m^3$). When the feedstock comprising halogenated organic compounds demonstrates thermal instability characteristics, it is preferred that the conversion temperatures be increased in stages to prevent decomposition of the feedstock on heat-exchange surfaces and catalyst by means of using two or more catalyst zones with interstage heating, for example.

In a preferred embodiment of the present invention, at least a portion of the hydrogen-rich gaseous stream which is introduced into the hydrogenation reaction zone which is used to hydrogenate the halogenated organic compound feed stream is provided via a recycle stream which is recovered from the hydrogenation zone which is utilized to hydrogenate the distillable hydrocarbonaceous compounds which are separated from the feedstock containing a non-distillable component.

In the event that the temperature of the halogen-containing organic feed stream is not deemed to be exactly the temperature selected to operate the catalytic hydrogenation zone, we contemplate that the temperature of the feed stream to be introduced into the hydrogenation zone may be adjusted either upward or downward in order to achieve the desired temperature in the catalytic hydrogenation zone. Such a temperature adjustment may be accomplished, for example, by either indirect heat exchange or by the addition of either cool or hot hydrogen.

The hydrogen-rich gaseous stream which is ultimately recovered from the effluent of the hydrogenation zone which is utilized to hydrogenate the feedstock comprising halogenated organic compounds in one embodiment of the present invention is recycled to the hot flash zone as described hereinabove.

Either of the hydrogenation zones utilized in the present invention may contain one or more catalyst zones. The preferred catalytic composites disposed within the hydrogenation zone which is utilized to hydrogenate the feedstock comprising halogenated organic compounds can be selected from the preferred catalytic composites which have been described hereinabove and are preferably used in the hydrogenation zone which is utilized to hydrogenate the distillable hydrocarbonaceous compounds which are separated from the non-distillable components.

The hydrocarbonaceous effluent from the hydrogenation zone utilized to hydrogenate a feedstock comprising halogenated organic compounds is preferably contacted with an aqueous scrubbing solution and the admixture is admitted to a separation zone in order to separate a halide-rich aqueous stream, a hydrogenated hydrocarbonaceous liquid phase and a hydrogen-rich gaseous phase which contains trace quantities of halogenated organic compounds. The contact of the hydrocarbonaceous effluent from the second hydrogenation zone with the aqueous scrubbing solution may be performed in any convenient manner and is preferably conducted by co-current, in-line mixing which may be promoted by inherent turbulence, mixing orifices or any other suitable mixing means. The aqueous scrubbing solution is preferably introduced in an amount from about 1 to about 100 vol. % of the total feedstock charged to the hydrogenation zone based on the quantity of hydrogen halide compounds present in the effluent from the hydrogenation zone. The aqueous scrubbing solution is selected depending on the characteristics of the organic feed stream introduced into the second hydrogenation zone. In accordance with the present invention, at least some halogenated organic compounds are introduced as feedstock and therefore the aqueous scrubbing solution in one embodiment preferably contains a basic compound such as calcium hydroxide, potassium hydroxide or sodium hydroxide in order to neutralize the acid such as hydrogen chloride, hydrogen bromide and hydrogen fluoride, for example, which is formed during the hydrogenation of the halogenated organic compounds. In another preferred embodiment, the halide component is recovered by dissolution in water or a lean aqueous solution of the halide compound. This embodiment permits the subsequent recovery and use of a desirable and valuable halide compound. The final selection of the aqueous scrubbing solution is dependent upon the particular halide compounds which are present and the desired end product. The resulting hydrogenated hydrocarbonaceous liquid phase is recovered and the hydrogen-rich gaseous phase is recycled in one embodiment. As described hereinabove, in one embodiment of the present invention, this recovered hydrogen-rich gaseous phase is heated and recycled to the flash zone and subsequently to the hydrogenation zone which is utilized to hydrogenate the distillable hydrocarbonaceous stream which is separated from the non-distillable component.

The resulting hydrogenated hydrocarbonaceous liquid phase is preferably recovered from the hydrogen-rich gaseous phase in the separation zone which is maintained at essentially the same pressure as the immediately preceding hydrogenation reaction zone and as a consequence contains dissolved hydrogen and low molecular weight normally gaseous hydrocarbons if present. In accordance with the present invention, it is preferred that the hydrogenated hydrocarbonaceous liquid phase comprising the hereinabove-mentioned gases be stabilized in a convenient manner, such as, for example, by stripping or flashing to remove the normally gaseous components to provide a stable hydrogenated distillable hydrocarbonaceous product. In some cases, we contemplate that a significant portion of the hydrogenated hydrocarbonaceous product may comprise methane, ethane, propane, butane, hexane and admixtures thereof. An adsorbent/stripper arrangement may conveniently be used to recover methane and ethane. Fractionation may conveniently be used to produce purified product streams such as liquid propane or LPG containing propane and butane.

In the drawing, the process of the present invention is illustrated by means of a simplified flow diagram in which such details as the total number of reaction zone vessels, pumps, instrumentation, heat-exchange and heat-recovery circuits, compressors and similar hardware have been deleted as being non-essential to an understanding of the techniques involved. The use of such miscellaneous appurtenances are well within the purview of one skilled in the art.

With reference now to the drawing, a liquid hydrocarbonaceous feed stream having a non-distillable component is introduced into the process via conduit 1 and is contacted with a hot gaseous hydrogen-rich recycle stream which is provided via conduit 26 and hereinafter described. The liquid hydrocarbonaceous feed stream and the hydrogen-rich recycle stream are introduced via conduit 26' and intimately contacted in hot hydrogen flash separator 2. A hydrocarbonaceous vapor stream comprising hydrogen is removed from hot hydrogen flash separator 2 via conduit 4 and introduced into hydrogenation reaction zone 5 without intermediate separation thereof. A heavy non-distillable stream is removed from the bottom of hot hydrogen flash separator 2 via conduit 3 and recovered. The resulting hydrogenated hydrocarbonaceous stream is removed from hydrogenation reaction zone 5 via conduit 6 and is introduced into hot separator 7. A liquid hydrocarbonaceous stream containing high molecular weight hydrocarbons are removed from hot separator 7 via conduit 8. A gaseous stream containing hydrogen and hydrocarbons having lower molecular weights are removed from hot separator 7 via conduit 9 and are contacted with an aqueous scrubbing solution which is introduced via conduit 10. The resulting admixture of the gaseous effluent from hot separator 7 and the aqueous scrubbing solution is passed via conduit 9 into vapor-liquid separator 11. A hydrogen-rich gaseous stream is removed from vapor-liquid separator 11 via conduit 14 and at least a portion of this stream is introduced via conduit 14 into guard bed 15. A fuel gas stream is removed from guard bed 15 via conduit 16 and recovered. At least a portion of the gaseous stream flowing in conduit 14 is diverted via conduit 17 and introduced into compressor 18 and the resulting compressed gas is transported from compressor 18 via conduit 17. Since hydrogen is lost in the process by means of a portion of the hydrogen being dissolved in the exiting liquid hydrocarbon streams and the hydrogen being consumed during the hydrogenation reactions, it is necessary to supplement the hydrogen-rich gaseous stream with make-up hydrogen from some suitable external source, for example, a catalytic reforming unit or a hydrogen plant. Make-up hydrogen may be introduced into the system at any convenient and suitable point, and is introduced in the drawing via conduit 19. A hydrocarbon stream containing lower molecular weight compounds is removed from vapor-liquid separator 11 via conduit 13 and recovered. A spent aqueous scrubbing solution is removed from vapor-liquid separator 11 via conduit 12 and recovered. A halogenated organic feed stream comprising halogenated organic compounds is introduced into the process via conduit 31 and is contacted with a hydrogen-rich gaseous recycle stream which is provided via conduit 17 and was hereinbefore described, and introduced into hydrogenation zone 20 via conduit 31. A recycle stream is provided via conduit 30 and is hereinafter described is also introduced into hydrogenation zone 20 via conduit 30 and conduit 31. The resulting hydrogenated stream is removed from hydrogenation reaction zone 20 via conduit 21, further heated in heat exchanger 32 and introduced into hydrogenation reaction zone 22. The resulting hydrogenated hydrocarbonaceous stream is removed from hydrogenation reaction zone 22 via conduit 23 and is contacted with an aqueous halide-lean scrubbing solution which is introduced via conduit 24. The resulting admixture of the hydrogenated hydrocarbonaceous effluent and the aqueous scrubbing solution is passed via conduit 23 and introduced into vapor-liquid separator 25. A hydrogen-rich gaseous stream which may contain small quantities of organic halide compounds is removed from vapor-liquid separator 25 via conduit 26 and passed through heat exchanger 27 to raise the temperature of the flowing stream. The resulting heated flowing stream is continued to be transported via conduit 26 and is subsequently introduced into hot flash separator 2 as described hereinabove. A halide-rich aqueous scrubbing solution is removed from vapor-liquid separator 25 via conduit 28 and recovered. A liquid hydrogenated hydrocarbonaceous stream comprising hydrogen in solution is removed from vapor-liquid separator 25 via conduit 29 and at least a portion of this stream is removed from the process and recovered. Another portion of the liquid hydrogenated hydrocarbonaceous stream which is removed from vapor-liquid separator 25 via conduit 29 is recycled via conduit 30 and conduit 31 to hydrogenation reaction zone 20 as described hereinabove. In the event that the liquid distillable hydrogenated hydrocarbonaceous product stream removed via conduit 29 contains propane, for example, and is therefore not accurately described as normally liquid, the vapor-liquid separator 25 may be necessarily operated at a pressure in the range from about 300 psig (2068 kPa gauge) to about 1000 psig (6895 kPa gauge).

The process of the present invention is further demonstrated by the following illustrative embodiment. This illustrative embodiment is, however, not presented to unduly limit the process of this invention, but to further illustrate the advantages of the hereinabove-described embodiments. The following data were not completely obtained by the actual performance of the present invention, but are considered prospective and reasonably illustrative of the expected performance of the invention.

ILLUSTRATIVE EMBODIMENT

A waste lube oil having the characteristics presented in Table 1 and contaminated with 20 ppm by weight of polychlorinated biphenyl (PCB) is charged at a rate of 100 mass units per hour to a hot hydrogen flash separation zone. The hot hydrogen is introduced into the hot hydrogen flash separation zone at a rate of 31 mass units per hour.

TABLE 1

| WASTE LUBE OIL FEEDSTOCK PROPERTIES | | |
|---|---|---|
| Specific Gravity @ 60° F. (15° C.) | 0.8827 | |
| Vacuum Distillation Boiling Range, (ASTM D-1160 | °F. | (°C.) |
| IBP | 338 | (170) |
| 10% | 516 | (269) |
| 20% | 628 | (331) |
| 30% | 690 | (367) |
| 40% | 730 | (388) |
| 50% | 750 | (399) |
| 60% | 800 | (421) |
| 70% | 831 | (444) |
| 80% | 882 | (474) |
| % Over | 80 | |
| % Bottoms | 20 | |
| Sulfur, weight percent | | 0.5 |
| Polychlorinated Biphenyl Concentration, wppm | | 20 |
| Lead, wppm | | 863 |
| Zinc, wppm | | 416 |
| Cadmium, wppm | | 1 |
| Copper, wppm | | 21 |
| Chromium, wppm | | 5 |

The waste lube oil is preheated to a temperature of <482° F. (<250° C.) before introduction into the hot hydrogen flash separation zone which temperature precluded any significant detectable thermal degradation. The waste lube oil is intimately contacted in the hot flash separation zone with a hot hydrogen-rich gaseous stream having a temperature upon introduction into the hot hydrogen flash separation zone of >748° F. (>398° C.). In addition, the hot hydrogen flash separation zone is operated at conditions which included a temperature of 788° F. (420° C.), a pressure of 810 psig (5585 kPa gauge), a hydrogen circulation rate of 18,000 SCFB (3034 normal $m^3/m^3$) and an average residence time of the vapor stream of 5 seconds.

A hydrocarbonaceous vapor stream comprising hydrogen is recovered from hot hydrogen flash separation zone, and is directly introduced without separation into a hydrogenation reaction zone containing a hydrogenation catalyst comprising alumina, nickel and molybdenum. Properties of $C_7^{30}$ fraction entering the reaction zone are presented in Table 2. The hydrogenation reaction is conducted with a catalyst peak temperature of 662° F. (350° C.), a pressure of 800 psig (5516 kPa gauge), a liquid hourly space velocity of 0.5 based on hydrocarbon feed to the hydrogenation reaction zone and a hydrogen to oil ratio of 20,000 SCFB (3370 normal $m^3/m^3$). The hydrogenated effluent from the hydrogenation reaction zone including small quantities of hydrogen chloride is passed into a hot flash zone to produce a heavy hydrocarbonaceous stream and a gaseous stream containing hydrogen, hydrogen chloride, hydrogen sulfide and lower molecular weight hydrocarbons which gaseous stream is contacted with an aqueous scrubbing solution containing sodium hydroxide, cooled to about 100° F. (38° C.), and sent to a vapor-liquid separator wherein a gaseous hydrogen-rich stream is separated from the normally liquid hydrocarbonaceous products and spent aqueous scrubbing solution containing sodium, sulfide and chloride ions. The resulting gaseous hydrogen-rich stream is bifurcated to provide a first stream which is passed through an adsorption zone to remove any trace quantities of organic halide compounds and to provide a fuel gas stream, and a second stream which is compressed and admixed with a fresh supply of hydrogen in an amount sufficient to maintain the hydrogenation reaction zone pressures.

TABLE 2

| PROPERTIES OF $C_7^+$ FRACTION OF REACTION ZONE FEED | | |
|---|---|---|
| Specific Gravity @ 60° F. (15° C.) | 0.866 | |
| Vacuum Distillation Boiling Range, (ASTM D-1160) | °F. | (°C.) |
| IBP | 225 | (107) |
| 10% | 433 | (223) |
| 20% | 538 | (280) |
| 30% | 633 | (334) |
| 40% | 702 | (372) |
| 50% | 741 | (394) |
| 60% | 770 | (410) |
| 70% | 801 | (427) |
| 80% | 837 | (447) |
| 90% | 896 | (479) |
| 95% | 943 | (506) |
| EP | 982 | (527) |
| % Over | 97 | |
| % Bottoms | 3 | |
| Sulfur, weight percent | | 0.31 |
| Polychlorinated Biphenyl Concentration, wppm | | 22 |
| Lead, wppm | | 3.7 |
| Zinc, wppm | | 1.5 |
| Cadmium, wppm | | <0.04 |
| Copper, wppm | | 0.1 |
| Chromium, wppm | | 0.6 |

A non-distillable liquid stream is recovered from the bottom of the flash separation zone in an amount of 12 mass units per hour and having the characteristics presented in Table 3.

TABLE 3

| ANALYSIS OF NON-DISTILLABLE STREAM | |
|---|---|
| Specific Gravity @ 60° F. (15° C.) | 0.95 |
| Polychlorinated Biphenyl Concentration, wppm | <2 |

A halogenated organic feedstock having the characteristics presented in Table 4 in an amount of 100 mass units per hour is admixed with hydrogen which is recycled from the first hydrogenation zone and the resulting admixture is charged to a second hydrogen zone containing a palladium on alumina catalyst which is conducted at hydrogenation conditions which include a maximum temperature of 572° F. (300° C.), a pressure of 850 psig (5860 kPa gauge) and a hydrogen to feed ratio of about 60,000 SCFB (10,110 normal $m^3/m^3$). A recycle stream containing hydrocarbons recovered from the second hydrogenation zone in an amount of 100 mass units per hour is also introduced to the second hydrogenation zone.

TABLE 4

| SATURATED, HALOGENATED HYDROCARBONACEOUS FEEDSTOCK PROPERTIES | |
|---|---|
| Specific Gravity @ 60° F. (15° C.) | 1.250 |
| Distillation, °C. | |
| IBP | 95 |

TABLE 4-continued

| SATURATED, HALOGENATED HYDROCARBONACEOUS FEEDSTOCK PROPERTIES | |
|---|---|
| 50% | 110 |
| EP | 259 |
| % Over | 97 |
| % Residue | 3 |
| Composition, Weight Percent | |
| Chlorinated Propenes | 44.0 |
| Chlorinated Propanes | 34.2 |
| Chlorinated Alcohols | 3.9 |
| Chlorinated Ethers | 10.0 |
| Chlorinated Hexadiene | 0.5 |
| Chlorinated Hexane | 1.1 |
| Chlorinated Benzene | 0.2 |
| Other | 6.1 |

The resulting effluent from the second hydrogenation reaction zone was neutralized with an aqueous solution containing potassium hydroxide and was found to contain 38 mass units of hydrocarbonaceous products having the characteristics presented in Table 5.

TABLE 5

| HYDROCARBONACEOUS PRODUCT STREAM PROPERTIES | |
|---|---|
| Composition, Weight Percent | |
| Ethane | 0.3 |
| Propane | 96.6 |
| Chlorinated Propane | Trace |
| Butane | Trace |
| Pentane | 0.0 |
| Hexane and Nonane | 3.1 |
| | 100.0 |

The foregoing description, drawing and illustrative embodiment clearly demonstrate the advantages encompassed by the process of the present invention and the benefits to be afforded with the use thereof.

What is claimed:

1. A process for the simultaneous hydrogenation of a first feedstock comprising hydrocarbonaceous compounds and having a non-distillable component, and a second feedstock comprising halogenated organic compounds which process comprises:

(a) contacting said first feedstock with a first hydrogen-rich gaseous stream having a temperature greater than said first feedstock in a flash zone at flash conditions thereby increasing the temperature of said first feedstock and vaporizing at least a portion thereof to provide a hydrocarbonaceous vapor stream comprising hydrogen, and a heavy product comprising said non-distillable component;

(b) contacting said hydrocarbonaceous vapor stream comprising hydrogen with a hydrogenation catalyst in a first hydrogenation reaction zone at hydrogenation conditions to increase the hydrogen content of said hydrocarbonaceous compounds contained in said hydrocarbonaceous vapor stream;

(c) condensing at least a portion of the resulting effluent from said first hydrogenation reaction zone to produce a second hydrogen-rich gaseous stream and a first liquid hydrogenated stream comprising hydrogenated distillable hydrocarbonaceous compounds;

(d) reacting said second feedstock comprising halogenated organic compounds and at least a portion of said second hydrogen-rich gaseous stream with a hydrogenation catalyst in a second hydrogenation reaction zone at hydrogenation conditions selected to produce hydrocarbonaceous compounds and at least one water-soluble inorganic halide compound;

(e) contacting the resulting effluent from said second hydrogenation zone containing hydrocarbonaceous compounds and at least one water-soluble inorganic halide compound with a halide-lean aqueous scrubbing solution;

(f) introducing a resulting admixture of said effluent from said second hydrogenation zone and said halide-lean aqueous scrubbing solution into a separation zone to provide a third hydrogen-rich gaseous stream, a second liquid hydrogenated stream comprising hydrocarbonaceous compounds and a halide-rich aqueous scrubbing solution containing at least a portion of said water-soluble inorganic halide compound;

(g) recycling and heating at least a portion of said third hydrogen-rich gaseous stream recovered in step (f) into step (a) as at least a portion of said first hydrogen-rich gaseous stream; and (h) recovering said first liquid hydrogenated stream comprising hydrogenated distillable hydrocarbonaceous compounds from step (c) and said second liquid hydrogenated stream comprising hydrocarbonaceous compounds from step (f).

2. The process of claim 1 wherein said first feedstock comprises dielectric fluids, hydraulic fluids, heat transfer fluids, used lubricating oil, used cutting oils, used solvents, still bottoms from solvent recycle operations, coal tars, atmospheric residuum, PCB-contaminated oils, halogenated wastes or other hydrocarbonaceous industrial waste.

3. The process of claim 1 wherein said non-distillable component comprises organometallic compounds, inorganic metallic compounds, finely divided particulate matter or non-distillable hydrocarbonaceous compounds.

4. The process of claim 1 wherein said first feedstock is introduced into said flash zone at a temperature less than about 482° F. (250° C).

5. The process of claim 1 wherein the temperature of said first hydrogen-rich stream is from about 200° F. (93° C.) to about 1200° F. (649° C).

6. The process of claim 1 wherein said flash conditions include a temperature from about 150° F. (65° C.) to about 860° F. (460° C.), a pressure from about atmospheric to about 2000 psig (13788 kPa gauge), a hydrogen circulation rate of about 1000 SCFB (168 normal $m^3/m^3$) to about 60,000 SCFB (10,110 normal $m^3/m^3$) based on said first feedstock, and an average residence time of said hydrocarbonaceous vapor stream comprising hydrogen in said flash zone from about 0.1 seconds to about 50 seconds.

7. The process of claim 1 wherein said first hydrogenation reaction zone is operated at conditions which include a pressure from about atmospheric (0 kPa gauge) to about 2000 psig (13790 kPa gauge), a maximum catalyst temperature from about 122° F. (50° C.) to about 850° F. (454° C.) and a hydrogen circulation rate from about 200 SCFB (3,7 normal $m^3/m^3$) to about 70,000 SCFB (11,796 normal std $m^3/m^3$).

8. The process of claim 1 wherein said first zone hydrogenation catalyst comprises a refractory inorganic oxide and at least one metallic compound having hydrogenation activity.

9. The process of claim 8 wherein said metallic compound is selected from the metals of Group VIB and VIII of the Periodic Table.

10. The process of claim 1 wherein at least a portion of the resulting effluent from said first hydrogenation zone is contacted with an aqueous scrubbing solution.

11. The process of claim 10 wherein said aqueous scrubbing solution comprises a compound selected from the group consisting of calcium hydroxide, potassium hydroxide, potassium carbonate, sodium carbonate and sodium hydroxide.

12. The process of claim 1 wherein said second feedstock comprises a component selected from the group consisting of fractionation column bottoms in the production of allyl chloride, fractionation column bottoms in the production of ethylene dichloride, fractionation column bottoms in the production of trichloroethylene and perchloroethylene, used dielectric fluid containing polychlorinated biphenyls (PCB) and chlorinated benzene, used chlorinated solvents, fractionation bottoms from the purification column in epichlorohydrin production, carbon tetrachloride, 1, 1, 1 trichloroethane, chlorinated alcohols, chlorinated ethers, chlorofluorocarbons, ethylene dibromide and mixtures thereof.

13. The process of claim 1 wherein said second hydrogenation zone is operated at conditions which include a pressure from about atmospheric (0 kPa gauge) to about 2000 psig (13790 kPa gauge), a maximum catalyst temperature from about 122° F. (50° C.) to about 850° F. (454° C.) and a hydrogen circulation rate from about 200 SCFB (33.7 normal $m^3/m^3$) to about 50,000 SCFB (8427 normal std $m^3/m^3$).

14. The process of claim 1 wherein said second hydrogenation zone catalyst comprises a refractory oxide and at least one metallic compound having hydrogenation activity.

15. The process of claim 14 wherein said metallic compound is selected from the metals of Group VIB and VIII of the Periodic Table.

16. The process of claim 1 wherein said halidelean aqueous scrubbing solution comprises a compound selected from the group consisting of calcium hydroxide, potassium hydroxide, potassium carbonate, sodium carbonate and sodium hydroxide.

17. The process of claim 1 wherein said second feedstock comprising halogenated organic compounds contain a halogen selected from the group consisting of chlorine, fluorine and bromine.

18. The process of claim 1 wherein said water-soluble inorganic halide compound is selected from the group consisting of hydrogen chloride and hydrogen fluoride.

* * * * *